United States Patent
Bourquin et al.

(10) Patent No.: US 11,992,263 B2
(45) Date of Patent: *May 28, 2024

(54) HAIR CUTTING DEVICE

(71) Applicant: KONINKLIJKE PHILIPS N.V., Eindhoven (NL)

(72) Inventors: Yannyk Parulian Julian Bourquin, Eindhoven (NL); Rieko Verhagen, Eindhoven (NL); Bastiaan Wilhelmus Maria Moeskops, Eindhoven (NL); Kiran Kumar Thumma, Eindhoven (NL); Joseph Petrus Henricus Ter Borch, Eindhoven (NL); Mark Thomas Johnson, Eindhoven (NL); Arnoldus Johannes Martinus Jozeph Ras, Eindhoven (NL); Gerhardus Wilhelmus Lucassen, Eindhoven (NL); Martinus Bernardus van der Mark, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/831,701

(22) Filed: Jun. 3, 2022

(65) Prior Publication Data
US 2022/0287773 A1  Sep. 15, 2022

Related U.S. Application Data

(63) Continuation of application No. 15/778,691, filed as application No. PCT/EP2016/081630 on Dec. 19, 2016, now Pat. No. 11,376,069.

(30) Foreign Application Priority Data

Dec. 22, 2015 (EP) .................................... 15202208

(51) Int. Cl.
A61B 18/20 (2006.01)
A61B 18/00 (2006.01)

(52) U.S. Cl.
CPC .. A61B 18/203 (2013.01); A61B 2018/00476 (2013.01); A61B 2018/202 (2013.01)

(58) Field of Classification Search
CPC ........ A61B 18/203; A61B 2018/00476; A61B 2018/00452; A61B 2018/2244;
(Continued)

(56) References Cited

U.S. PATENT DOCUMENTS

| 5,359,681 A | 10/1994 | Jorgenson |
| 5,735,844 A | 4/1998 | Anderson |

(Continued)

FOREIGN PATENT DOCUMENTS

| JP | 2006198041 A | 8/2006 |
| WO | 9623447 A1 | 8/1996 |

(Continued)

OTHER PUBLICATIONS

M.D. Greenwell, A. Willner, Paul L. Kirk, Human Hair Studies: III. Refractive Index of Crown Hair 31 Am. Inst. Crim. L. & Criminology 746 (1940-1941).

(Continued)

*Primary Examiner* — Jon Eric C Morales

(57) ABSTRACT

A hair cutting device for cutting hair on a body of a subject includes a light source for generating laser light at one or more specific wavelengths corresponding to wavelengths absorbed by one or more chromophores in hair; and a cutting element that has an optical waveguide that is coupled to the light source to receive laser light. A portion of a side wall of the optical waveguide forms a cutting face for contacting hair where, at least at the cutting face, the optical waveguide has a refractive index that is equal to or lower than the (Continued)

refractive index of hair and higher than the refractive index of skin.

23 Claims, 4 Drawing Sheets

(58) Field of Classification Search
CPC .. A61B 2018/2261; A61B 2018/00601; A61B 2017/00747; A61B 2017/00761; A61B 2018/202; A61B 18/20; A61B 2090/036; A61N 5/0616; A61N 5/0617
See application file for complete search history.

(56) References Cited

U.S. PATENT DOCUMENTS

| | | |
|---|---|---|
| 9,017,322 B2 | 4/2015 | Gustavsson |
| 2008/0244912 A1 | 10/2008 | Gustavsson |
| 2012/0123444 A1 | 5/2012 | Verhagen |
| 2014/0276685 A1 | 9/2014 | Gustavsson |
| 2015/0051593 A1 | 2/2015 | Johnson |
| 2017/0209213 A1 | 7/2017 | Binun |

FOREIGN PATENT DOCUMENTS

| | | |
|---|---|---|
| WO | 9907438 A1 | 2/1999 |
| WO | 0009023 A1 | 2/2000 |
| WO | 2004073537 A2 | 9/2004 |
| WO | 2005065565 A1 | 7/2005 |
| WO | 2009074957 A1 | 6/2009 |
| WO | 2011010246 A1 | 1/2011 |
| WO | 2014143670 A1 | 9/2014 |
| WO | 2017/079339 | 5/2017 |

OTHER PUBLICATIONS

Huafeng Ding et al., "Refractive indices of human skin tissues at eight wavelengths and estimated dispersion relations between 300 and 1600 nm", 2006 Phys. Med. Biol. 51 1479.

HAIR CUTTING DEVICE

CROSS-REFERENCE TO PRIOR APPLICATIONS

This application is a continuation of U.S. application Ser. No. 15/778,691, filed on May 24, 2018, which is the U.S. National Phase application under 35 U.S.C. § 371 of International Application No. PCT/EP2016/081630, filed on Dec. 19, 2016, which claims the benefit of European Application No. 15202208.3 filed on Dec. 22, 2015. These applications are hereby incorporated by reference herein.

FIELD OF THE INVENTION

The invention relates to a hair cutting device for cutting (e.g. shaving) hair on a body of a subject, and in particular relates to a hair cutting device that uses laser light to cut or shave hair.

BACKGROUND OF THE INVENTION

Shaving devices for cutting or shaving hair on a body of a subject typically make use of one or more blades that cut hairs as the blade is moved across the skin of the subject. The blades can be static within the device, for example as in a wet razor, whereas in other types of devices, for example electric shavers, one or more blade elements can be actuated (e.g. rotated or oscillated) in order to produce a cutting action.

However, an alternative type of shaving device has been proposed in WO 2014/143670 that makes use of laser light. In particular a laser light source is provided that is configured to generate laser light having a wavelength selected to target a predetermined chromophore to effectively cut a hair shaft. A fiber optic is located on a shaving portion of the device that is positioned to receive the laser light from the laser light source at a proximal end, conduct the laser light from the proximal end toward a distal end, and emit the light out of a cutting region of the fiber optic and toward hair when the cutting region is brought in contact with the hair.

SUMMARY OF THE INVENTION

To achieve good shaving closeness, the cutting element of the shaving device (i.e. the fiber optic in the case of the device in WO 2014/143670) needs to be brought very close to the skin or even touch the skin. That device is made in such way that the light couples into a hair when a hair is in contact with the fiber optic. In particular, this is achieved by the core of the fiber optic having a lower refractive index than hair. However, since the refractive index of skin is close to the refractive index of hair, the laser light will also be able to couple into the skin if the cutting element is brought into contact with the skin. This will potentially lead to burning of the skin and create a significant safety issue for this type of shaving device.

Although WO 2014/143670 describes that the risk of a subject accidentally contacting another portion of the body with a light emitting portion of the fiber optic can be reduced by creating the cutting element by removing the cladding of the fiber optic from only a portion of the circumference of the fiber (which should allow the fiber to touch the skin where the cladding is thicker and prevent energy being coupled into the skin while allowing the fiber to touch the hair where the cladding is thinner or the core exposed). Although this method seems reasonable, in reality the skin cannot be considered as a solid flat surface, and moving fiber across the skin will induce skin doming and bulging, and consequently the skin will enter into contact with the thin cladding region (or exposed core) and the laser light will cause burning of the skin.

Therefore there is a need for an improved hair cutting device that reduces the risk of damage or injury to the skin of the subject.

According to a first aspect, there is provided a hair cutting device for cutting hair on a body of a subject, the hair cutting device comprising a light source for generating laser light at one or more specific wavelengths corresponding to wavelengths absorbed by one or more chromophores in hair; and a cutting element that comprises an optical waveguide that is coupled to the light source to receive laser light, wherein a portion of a side wall of the optical waveguide forms a cutting face for contacting hair, and wherein at least at the cutting face the optical waveguide has a refractive index that is equal to or lower than the refractive index of hair and higher than the refractive index of skin.

In some embodiments, the refractive index of the optical waveguide at the cutting face is equal to or higher than 1.48, optionally equal to or higher than 1.50, optionally equal to or higher than 1.51, optionally equal to or higher than 1.52, optionally equal to or higher than 1.53, optionally equal to or higher than 1.54.

In some embodiments, the refractive index of the optical waveguide at the cutting face is equal to or lower than 1.56, optionally equal to or lower than 1.55, optionally equal to or lower than 1.54.

In some embodiments, the refractive index of the optical waveguide at the cutting face is in the range 1.48-1.56, optionally in the range 1.51-1.55, optionally in the range 1.53-1.54.

In some embodiments, the optical waveguide is composed of or comprises silica, fluoride glass, phosphate glass, chalcogenide glass, and/or crown glass.

In some embodiments, the optical waveguide comprises a core, and the cutting face is a portion of the side wall of the core.

In alternative embodiments, the optical waveguide comprises a core and a cladding surrounding the core, and the cutting face is a portion of the side wall of the cladding. In these embodiments, the refractive index of the core can be lower than or equal to the refractive index of the hair and higher than the refractive index of the skin, and the refractive index of the cladding can be lower than the refractive index of the core. In these embodiments, the cutting face can comprise a portion of the cladding that is thinner than the cladding on other portions of the optical waveguide.

In some embodiments, the optical waveguide is a D-shape optical waveguide or a polished optical waveguide.

In alternative embodiments, the optical waveguide comprises a core and cladding that partially covers the core, and the cutting face comprises the portion of the core that is not covered by the cladding.

In alternative embodiments, the refractive index of the optical waveguide decreases with increasing distance from an optical axis of the optical waveguide, and the cutting face is a shorter distance from the optical axis than other portions of the optical waveguide.

In some embodiments, a second portion of the side wall of the optical waveguide forms a skin interface for contacting the skin of the subject while the cutting interface is contacting hair, and the refractive index of the optical waveguide at the skin interface is higher than the refractive index of skin.

In some embodiments, the optical waveguide comprises a core and a cladding that partially surrounds the core, and the cutting face is formed in a side wall of the core and the second portion of the side wall is formed in a side wall of the cladding.

In preferred embodiments the optical waveguide is an optical fibre.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

As noted above, the present invention provides an improvement in the safety and comfort of a subject that is using a laser light-based shaving device described in WO 2014/143670. In particular, it has been recognised that by selecting an optical fibre for the cutting element that has a refractive index that is equal to or lower than the refractive index of hair and higher than the refractive index of skin, laser light can couple into hair when hair is in contact with the optical fibre, but light will not be able to couple into the skin, thereby reducing the risk of burning or irritating the skin of the subject.

It will be appreciated that the invention is applicable to shaving devices (e.g. razors or electric shavers), and any other type of device that is used to cut hair (e.g. hair clippers), even if those devices do not necessary aim to provide a 'clean shave' (i.e. to remove hair at the level of the skin).

Figure 1:
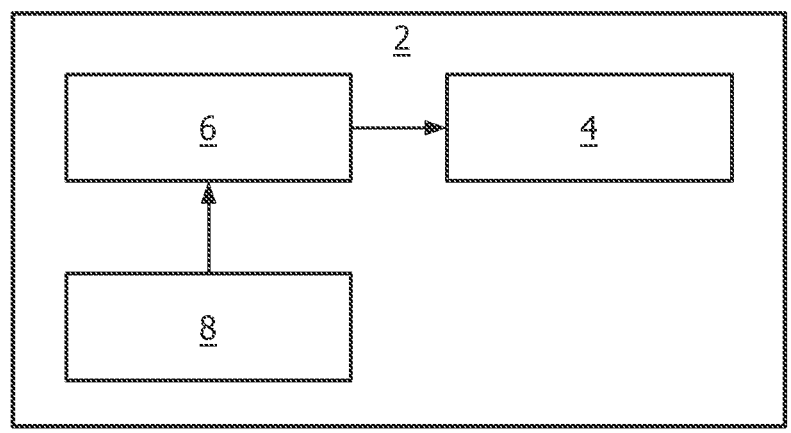
FIG. 1 is a block diagram of a hair cutting device according to an embodiment of the invention.
Figure 2:
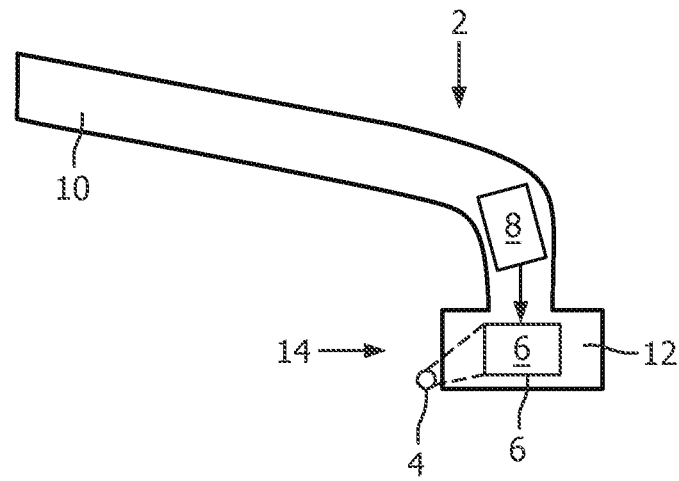
FIG. 2 is a pair of schematic drawings showing different views of an exemplary hair cutting device according to an embodiment of the invention.
Figure 2:
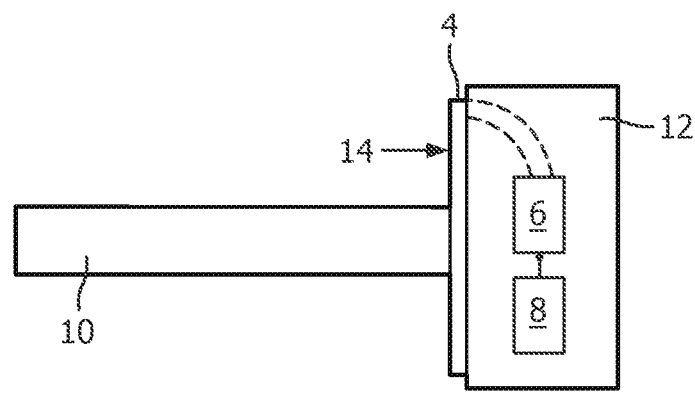

FIG. 1 is a block diagram of a hair cutting device 2 according to an embodiment of the invention. FIG. 2 shows a hair cutting device 2 in the form of a handheld razor according to an exemplary embodiment of the invention. The hair cutting device 2 is for cutting (e.g. shaving) hair on a body of a subject. The subject may be a person or an animal. The hair may be facial hair (i.e. hair on the subject's face), or hair on the subject's head or other part of their body (legs, chest, etc.).

The hair cutting device 2 comprises a cutting element 4 that enables hair to be cut as the hair cutting device 2 is moved over the skin of a subject. The cutting element 4 is an optical waveguide 4 that is arranged on the hair cutting device 2 so that the optical axis of the optical waveguide 4 (i.e. the line along which light typically propagates through the optical waveguide 4) is generally perpendicular to the direction in which the hair cutting device 2 is moved so that hairs contact the side wall of the optical waveguide 4 (the side wall corresponding to the long edge of the optical waveguide 4) as the hair cutting device 2 is moved across the skin of the subject. In the following description of the embodiments of the invention, the optical waveguide is an optical fibre 4, although those skilled in the art will be aware of other types of optical waveguide that can be used according to the invention, such as a slab waveguide, a strip waveguide or a photonic crystal waveguide.

A light source 6 is provided in the hair cutting device 2 that generates laser light at one or more specific wavelengths. The light source 6 is optically coupled to the optical fibre 4 so that the laser light generated by the light source 6 is coupled into the optical fibre 4 (and specifically coupled into an end of the optical fibre 4 so that the laser light propagates through the optical fibre 4).

The light source 6 is configured to generate laser light at one or more specific wavelengths that can be used to cut or burn through hair. In particular, each wavelength corresponds to the wavelength of light absorbed by a chromophore that is found in hair. As is known, a chromophore is the part of a molecule that provides the molecule with its colour. Thus, the laser light will be absorbed by the chromophore and converted into heat which will melt or burn the hair or otherwise destroy the bonds in the molecules of the hair.

Suitable chromophores that can be targeted by the laser light generated by the light source 6 include, but are not limited to, melanin, keratin and water. Suitable wavelengths of laser light that can be used include, but are not limited to, wavelengths selected from the range 380 nm (nanometers) to 500 nm and 2500 nm to 3500 nm. Those skilled in the art will be aware of the wavelengths of light that are absorbed by these chromophores, and thus also the specific wavelengths of light that the light source 6 should generate for this purpose, and further details are not provided herein.

In some embodiments the light source 6 can be configured to generate laser light at a plurality of wavelengths (either simultaneously or sequentially), with each wavelength being selected to target a different type of chromophore. This can improve the cutting action of the optical fibre 4 since multiple types of molecules in the hair may be burnt using the laser light. Alternatively multiple light sources 6 can be provided that each generate laser light at a respective wavelength, and each light source 6 can be coupled to a respective optical fibre 4 to provide multiple cutting elements 4 in the device 2.

The hair cutting device 2 also comprises a control unit 8 that controls the operation of the hair cutting device 2, and in particular is connected to the light source 6 to control the activation and deactivation of the light source 6 (and in some embodiments control the wavelength and/or intensity of the light generated by the light source 6). The control unit 8 may activate and deactivate the light source 6 in response to an input from a user of the hair cutting device 2. The control unit 8 can comprise one or more processors, processing units, multi-core processors or modules that are configured or programmed to control the hair cutting device 2.

As noted above, FIG. 2 shows a hair cutting device 2 that is in the form of a handheld wet razor. FIG. 2 shows a side view and a bottom view of the razor 2. The razor 2 comprises a handle 10 for the subject (or other user of the device 2) to hold, and a head portion 12 that includes the cutting element 4 (optical fibre). As shown, the optical fibre 4 is arranged along an edge of the head portion, and a part of the optical fibre 4 forms (or corresponds to) a cutting face 14. The cutting face 14 is the part of the optical fibre 4 that is intended to come into contact with hair as the hair cutting device 2 is moved across the skin of the subject. A light source 6 and control unit 8 are shown as being incorporated into the head portion 12 and handle 10 respectively, but it will be appreciated that the positions of these components in the hair cutting device 2 as shown in FIG. 2 is not limiting. Likewise it will be appreciated that the embodiment shown in FIG. 2 is merely an example, and the invention can be incorporated or used in any type of hair cutting device 2 that conventionally comprises a blade for physically cutting or slicing hair (whether the blade is static or actuated in order to achieve a cutting action).

Figure 3:
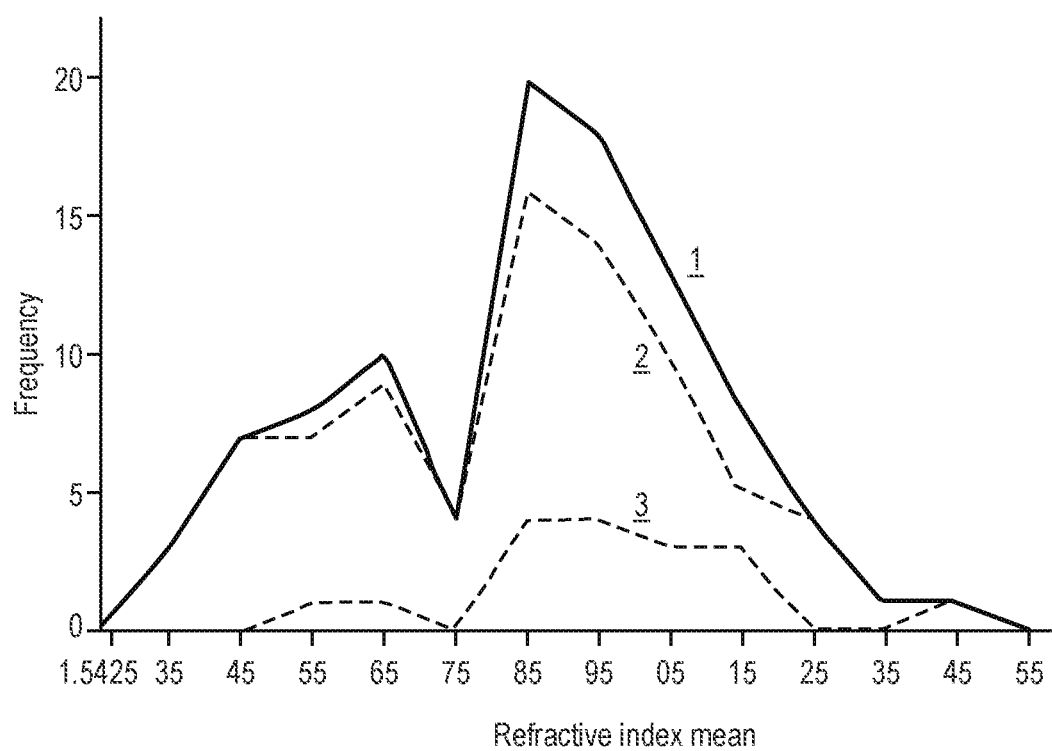
FIG. 3 is a graph illustrating the refractive index of hair.

The graph in FIG. 3 illustrates the refractive index of hair, which can be found in a paper by M. D. Greenwell, A. Willner, Paul L. Kirk: Human Hair Studies: III. Refractive Index of Crown Hair, 31 Am. Inst. Crim. L. & Criminology 746 (1940-1941). Curve 1 is a composite line, curve 2 is a line representing the refractive index for Caucasian people, and curve 3 is a line representing the refractive index for non-Caucasian people. Thus, it can be seen that the refractive index of hair is between (approximately) 1.545 and 1.555, although there will be variation between individuals. For example the above paper also recognises that the refractive index of hair can depend on the sex of the subject, e.g. the refractive index of hair on a female is generally higher than the refractive index of hair on a male.

As is known, the optical fibre 4 acts as a waveguide for the light coupled from the light source 6 through the occurrence of total internal reflection, since the refractive index of air is lower than that of the optical fibre 4. However, if an object that has a refractive index higher than the optical fibre 4 is put into contact with the optical fibre 4, then the total internal reflection is 'frustrated' and light can couple from the optical fibre 4 into that object. Thus, in order for light to be coupled into a hair from the optical fibre 4 (to provide the cutting action according to the invention), the optical fibre 4 must have the same or a lower refractive index than hair at the point at which the hair contacts the optical fibre 4. Thus, the optical fibre 4 must have the same or a lower refractive index than hair at least at the cutting face 14 portion of the optical fibre 4. Preferably the refractive index of the optical fibre 4 at the cutting face 14 is the same as that of hair since that provides the best coupling of light from the optical fibre 4 to the hair.

Thus, in some embodiments, the refractive index of the optical fibre 4 at least at the cutting face 14 is equal to or lower than 1.56. More preferably the refractive index of the optical fibre 4 at least at the cutting face 14 is equal to or lower than 1.55. Even more preferably, the refractive index of the optical fibre 4 at least at the cutting face 14 is equal to or lower than 1.54, since this refractive index is below the refractive indices identified in FIG. 3.

Figure 4:
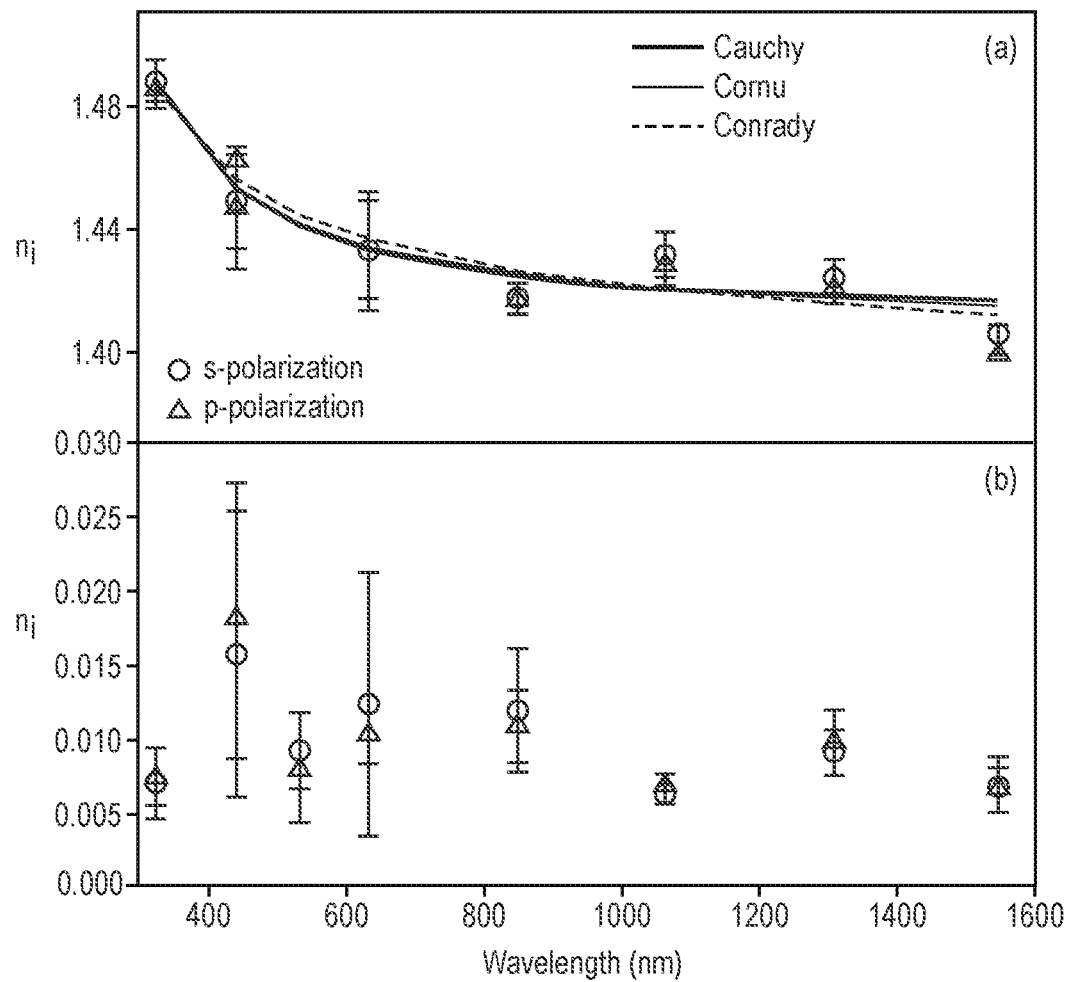
FIG. 4 is a graph illustrating the refractive index of the epidermis layer of skin.

The graph in FIG. 4, which is found in the paper "Refractive indices of human skin tissues at eight wavelengths and estimated dispersion relations between 300 and 1600 nm" by Huafeng Ding et al., 2006 Phys. Med. Biol. 51 1479, illustrates the real and imaginary refractive indices of human skin (specifically the upper layer of skin—the epidermis) versus wavelength (graphs (a) and (b) respectively). Each data point and associated error bar is the mean and standard deviation obtained from 12 or 18 measurements of 4 or 6 skin samples.

Thus, it can be seen that the refractive index of the epidermis varies from around 1.47 at the shorter wavelengths of light that can be used to target chromophores (e.g. 380 nm to 500 nm), down to around 1.42 at longer wavelengths.

Therefore, to avoid (or at least substantially reduce the risk) of laser light coupling into the skin when the skin contacts the optical fibre 4, at the cutting face 14 the optical fibre 4 should have a refractive index that is above that of skin to avoid the contact between the cutting face 14 and the skin causing frustrated total internal reflection in the optical fibre 4. Preferably the optical fibre 4 should have a refractive index that is above that of the epidermis layer of the skin. Even more preferably, the optical fibre 4 should have a refractive index that is above that of the stratum corneum, which is the uppermost layer of the epidermis, and is the part that will be in contact with the optical fibre 4. The stratum corneum has a refractive index that varies depending on hydration level and the presence of other substances (creams, oils, etc.) and is in the range 1.5 to 1.54.

Thus, based on the data shown in FIG. 4, in some embodiments, the refractive index of the optical fibre 4 at least at the cutting face 14 is equal to or higher than 1.48. More preferably the refractive index of the optical fibre 4 at least at the cutting face 14 is equal to or higher than 1.50. Even more preferably, the refractive index of the optical fibre 4 at least at the cutting face 14 is equal to or higher than 1.51. Even more preferably, the refractive index of the optical fibre 4 at least at the cutting face 14 is equal to or higher than 1.52 or 1.53. Even more preferably, the refractive index of the optical fibre f4 at least at the cutting face 14 is equal to or higher than 1.54.

It will be appreciated that it is preferable for the refractive index of the optical fibre 4 to be as high as possible relative to that of skin to avoid or reduce the risk of light coupling to the skin.

Thus, following the embodiments set out above, in some embodiments the refractive index of the optical fibre 4 at the cutting face 14 can be selected from the range 1.48-1.56, or more preferably from the range 1.51-1.55, or even more preferably from in the range 1.53-1.55 or 1.54-1.55.

It will be appreciated that in some embodiments the selection of the specific refractive index for the optical fibre 4 may also take into account the wavelength of the laser light that will be used to generate the cutting action, since the refractive index of the skin varies with the wavelength of incident light as shown in FIG. 4.

The optical fibre 4 can be made from any suitable material or combination of materials. For example optical fibre can be composed of or comprise silica, fluoride glass, phosphate glass, chalcogenide glass, and/or crown glass (such as BK7).

Figure 5:
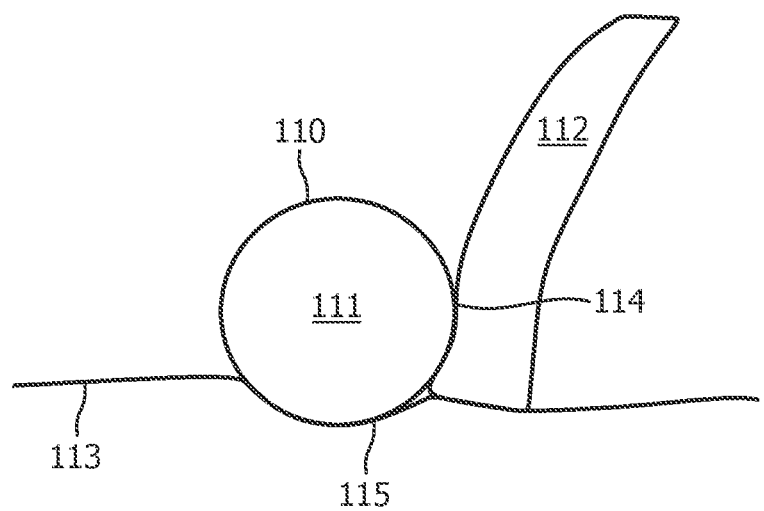
FIG. 5 is an illustration of an optical fibre cutting element according to a first specific embodiment.
Figure 6:
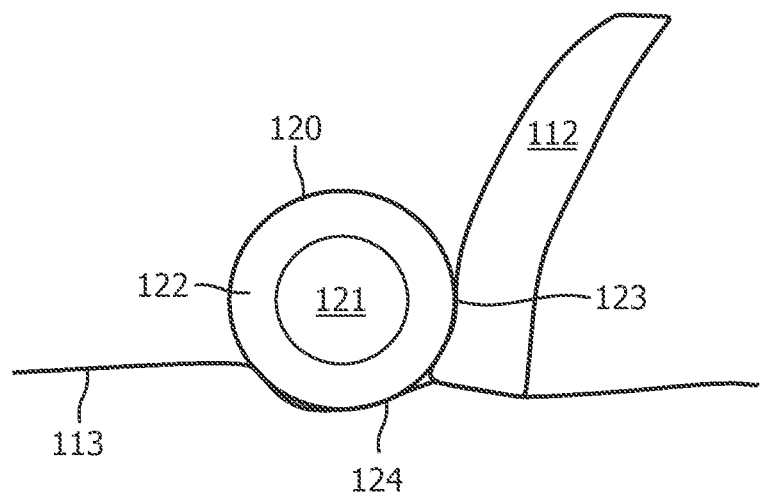
FIG. 6 is an illustration of an optical fibre cutting element according to a second specific embodiment.
Figure 7:
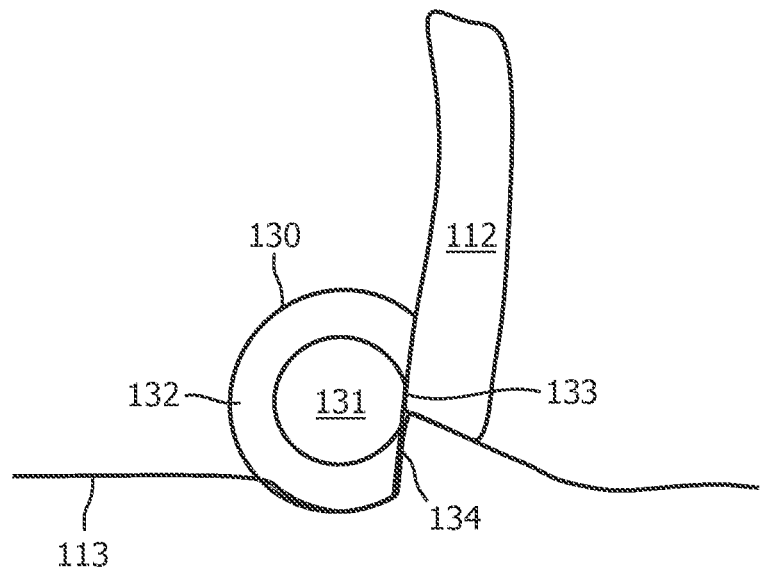
FIG. 7 is an illustration of an optical fibre cutting element according to a third specific embodiment.

FIGS. 5, 6 and 7 illustrate three exemplary embodiments of the cutting element 4 (optical fibre 4) according to the invention. In each of FIGS. 5, 6 and 7, only the optical fibre 4 part of the hair cutting device 2 is shown, and the optical fibre 4 is shown side on (i.e. looking down the optical axis of the optical fibre 4).

In FIG. 5, an optical fibre 110 is shown that has a core 111. This optical fibre 110 does not include any cladding around the core 111. The optical fibre 110 is shown in contact with a hair 112 and the skin 113. A portion of the side wall of the core 111/optical fibre 110 that is intended to contact hairs during use forms a cutting face 114. In accordance with the teaching above, the refractive index of the core 111 is the same or lower than the refractive index of hair and above the refractive index of skin (and thus the refractive index of the core 111 can take any of the exemplary values of the refractive index set out above), and thus, for example, the refractive index can be selected from the range 1.48-1.56, or more preferably from the range 1.51-1.55, or even more preferably from in the range 1.53-1.55 or 1.54-1.55.

Therefore, while in contact with the hair 112 at cutting face 114 and the skin 113 at interface 115, the laser light is coupled through the cutting face 114 into the hair 112 as the refractive index of the core 111 at cutting face 114 is smaller than the refractive index of the hair 112. However, the light is not coupled from the core 111 to the skin 113 through the skin interface 115 as the refractive index of the core 111 at interface 115 is larger than the refractive index of the skin 113. An evanescent field is likely to be present at the interface 115, from which the energy decays exponentially with the distance from the core 111, thus the energy delivered to the skin 113 is too low to damage the skin 113.

The core 111 may have a uniform refractive index (i.e. the same refractive index throughout the core 111), or it may be a graded index fibre, which means that the refractive index decreases with increasing distance from the optical axis. In either case, if the optical fibre 110 has a circular cross section, then the refractive index at the cutting face 114 and interface 115 will be the same as each other. As noted below, in some embodiments the optical fibre 110 may not have a circular cross-section, and the optical fibre 110 may be shaped such that the refractive index of the fibre 110 at the skin interface 115 is higher than the refractive index of the fibre 110 at the cutting face 114.

In FIG. 6, an optical fibre 120 is shown that has a core 121 and a cladding 122 that surrounds the core 121. The refractive index of the core 121 is lower than or equal to the refractive index of the hair 112 but higher than the refractive index of the skin 113. The refractive index of the cladding 122 is lower than or equal to the refractive index of the hair 112 and lower than the core 121 and higher than the refractive index of the skin 113.

The optical fibre 120 is shown in contact with a hair 112 and the skin 113. A portion of the side wall of the cladding 122 that is intended to contact hairs during use forms a cutting face 123. In accordance with the teaching above, the refractive index of the cladding 122 is lower than or equal to the refractive index of the hair 112 and lower than the core 121 and higher than the refractive index of the skin 113. The cladding 122 may be thick or thin (relative to the diameter of the core 121). In this embodiment the cladding 122 prevents loss of energy through the skin interface 124 between the optical fibre 120 and the skin 113 via the evanescent field generated at the interface between the core 121 and the cladding 122.

Conventionally, cladding 122 is provided in order to help keep the light in the core 121. However, in this embodiment it is desired for light to couple from the core 121 to the hair 112 via the cladding 122. One way in which this can be enabled is through the presence of a very thin layer of cladding (just at the cutting face 123, or across the whole optical fibre 120). In particular, the cladding 122 should be thinner than the distance of the evanescent field generated by the light in the core 121. Thus the light would still be able to couple into a material having a higher refractive index but the evanescent field in a material having a lower refractive index would be decreased to further reduce possibility of scattering/absorption in the skin 113. Another way in which this coupling from the core 121 to the hair 112 via the cladding 122 can be enabled is to construct the optical fibre 120 so that light is directed to travel in the cladding 122 rather than the core 121 in a certain portion of the optical fibre 120 (e.g. in a case where a tapered fibre is used). An optical fibre according to this embodiment can be easier to fabricate than the fibres used in other embodiments.

In the embodiment of FIG. 7, the optical fibre 130 has a non-circular cross section. In particular, the optical fibre 130 comprises a core 131 and a cladding 132 that partially surrounds the core 131. A cutting face 133 is formed by an exposed part of the core 131, or by a part of the optical fibre 130 where the cladding 132 is much thinner than elsewhere on the optical fibre 130. During normal use (i.e. where the cutting face 133 contacts hairs), the optical fibre 130 will contact skin 113 at a skin interface 134 where there is cladding 132 (or a thicker layer of cladding 132) between the core 131 and the skin 113.

In some embodiments the optical fibre 130 may have been formed with the cladding 132 completely surrounding the core 131, and the cladding 132 is then polished or otherwise shaped to partially or completely remove the cladding 132 along a part of the side wall of the optical fibre 130 to form a cutting face 133. Alternatively the cladding 132 may only have been formed around part of the core 131 so as to leave a part of the side wall of the core 131 exposed as the cutting face 133. The optical fibre 130 may be a D-shape type of fibre 130.

In accordance with the teachings above, the refractive index of the core 131 is larger than that of skin 113 so if the skin 113 contacts the cutting face 133 or contacts the cladding at skin interface 134, laser light is not coupled to the skin. In this embodiment, the refractive index of the cladding 132 is preferably higher than the refractive index of the skin 113, but in some embodiments the refractive index of the cladding 132 may be lower than the skin (since in this case the refractive index of the cladding 132 is selected such that light from the core 131 does not couple into the cladding 132).

In another embodiment, which can be combined with the non-circular cross section embodiment in FIG. 7, the optical fibre 4 can be a graded index fibre which means that the refractive index decreases with increasing distance from the optical axis. In this embodiment, the optical fibre 4 can be shaped so that the cutting face 14 is further from the optical axis than a skin interface, and the cutting face 14 is such that the refractive index at the cutting face 14 is equal to or lower than the refractive index of hair and higher than the refractive index of skin, while being lower than the refractive index at the skin interface.

There is therefore provided an improved hair cutting device that has a reduced risk of causing damage or injury to the skin of the subject.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A hair cutting device for cutting hair on a body of a subject, the hair cutting device comprising: a light source for generating laser light at one or more specific wavelengths corresponding to wavelengths absorbed by one or more chromophores in hair; and a cutting element that comprises an optical waveguide that is coupled to the light source to receive laser light, wherein a portion of a side wall of the optical waveguide forms a cutting face for contacting hair, and wherein the optical waveguide at the cutting face has a refractive index in a range of 1.48-1.56.

2. The hair cutting device as claimed in claim 1, wherein the refractive index of the optical waveguide at the cutting face is equal to or higher than 1.50.

3. The hair cutting device as claimed in claim 1, wherein the refractive index of the optical waveguide at the cutting face is equal to or higher than 1.51.

4. The hair cutting device as claimed in claim 1, wherein the refractive index of the optical waveguide at the cutting face is equal to or higher than 1.52.

5. The hair cutting device as claimed in claim 1, wherein the refractive index of the optical waveguide at the cutting face is equal to or higher than 1.53.

6. The hair cutting device as claimed in claim 1, wherein the refractive index of the optical waveguide at the cutting face is equal to or higher than 1.54.

7. The hair cutting device as claimed in claim 1, wherein the refractive index of the optical waveguide at the cutting face is equal to or lower than 1.55.

8. The hair cutting device as claimed in claim 1, wherein the refractive index of the optical waveguide at the cutting face is equal to or lower than 1.54.

9. The hair cutting device as claimed in claim 1, wherein the refractive index of the optical waveguide at the cutting face is in the range 1.51-1.55.

10. The hair cutting device as claimed in claim 1, wherein the refractive index of the optical waveguide at the cutting face is in the range 1.53-1.54.

11. The hair cutting device as claimed in claim 1, wherein the optical waveguide is composed of or comprises silica, fluoride glass, phosphate glass, chalcogenide glass, and/or crown glass.

12. The hair cutting device as claimed in claim 1, wherein the optical waveguide comprises a core and a cladding surrounding the core, wherein the cutting face is a portion of the side wall of the cladding.

13. The hair cutting device as claimed in claim 12, wherein the refractive index of the core is lower than or equal to the refractive index of the hair and higher than the refractive index of the skin, and wherein the refractive index of the cladding is lower than the refractive index of the core.

14. The hair cutting device as claimed in claim 12, wherein the cutting face comprises a portion of the cladding that is thinner than the cladding on other portions of the optical waveguide.

15. The hair cutting device as claimed in claim 12, wherein the optical waveguide is a D-shape optical waveguide or a polished optical waveguide.

16. The hair cutting device as claimed in claim 1, wherein the optical waveguide comprises a core and cladding that partially covers the core, wherein the cutting face comprises the portion of the core that is not covered by the cladding.

17. The hair cutting device as claimed in claim 1, wherein the refractive index of the optical waveguide decreases with increasing distance from an optical axis of the optical waveguide, wherein the cutting face is a shorter distance from the optical axis than other portions of the optical waveguide.

18. The hair cutting device as claimed in claim 1, wherein the optical waveguide is an optical fibre.

19. A hair cutting device for cutting hair on a body of a subject, the hair cutting device comprising:
   a light source for generating laser light at one or more specific wavelengths corresponding to wavelengths absorbed by one or more chromophores in hair; and
   a cutting element that comprises an optical waveguide that is coupled to the light source to receive laser light, wherein the optical waveguide comprises a core and a cladding surrounding the core,
   wherein:
      a refractive index of the cladding is lower than a refractive index of the core, a portion of a side wall of the optical waveguide forms a cutting face for contacting hair,
      the cutting face is a portion of the side wall of the cladding and comprises a portion of the cladding that is thinner than the cladding on other portions of the optical waveguide, and
      the optical waveguide at the cutting face has a refractive index in a range of 1.48-1.56 so as to be equal to or lower than a refractive index of hair and higher than a refractive index of skin.

20. The hair cutting device as claimed in claim 19, wherein the optical waveguide is composed of or comprises silica, fluoride glass, phosphate glass, chalcogenide glass, and/or crown glass.

21. The hair cutting device as claimed in claim 19, wherein the refractive index of the core is lower than or equal to the refractive index of the hair and higher than the refractive index of the skin.

22. The hair cutting device as claimed in claim 19, wherein the optical waveguide is a D-shape optical waveguide or a polished optical waveguide.

23. The hair cutting device as claimed in claim 19, wherein the refractive index of the optical waveguide at the cutting face is in the range of 1.48-1.54.

* * * * *